(12) United States Patent
Stearns et al.

(10) Patent No.: US 6,247,731 B1
(45) Date of Patent: Jun. 19, 2001

(54) NUT WITH CONTROLLED INTERNAL RADIUS

(75) Inventors: Stanley D. Stearns; Herbert Max Loy, Jr., both of Houston, TX (US)

(73) Assignee: Valco Instruments Company, Inc., Houston, TX (US)

( * ) Notice: Subject to any disclaimer, the term of this patent is extended or adjusted under 35 U.S.C. 154(b) by 0 days.

(21) Appl. No.: 09/368,365

(22) Filed: Aug. 4, 1999

(51) Int. Cl.[7] .................................................. F16L 35/00
(52) U.S. Cl. ................................ 285/353; 285/384
(58) Field of Search ................................ 285/353, 384, 285/383, 114

(56) References Cited

U.S. PATENT DOCUMENTS

| | | | | |
|---|---|---|---|---|
| 2,457,384 | * | 12/1948 | Krenz ..................................... | 285/353 |
| 2,952,481 | * | 9/1960 | Weatherhead .......................... | 285/353 |
| 4,516,278 | * | 5/1985 | Lamond ................................. | 285/387 |
| 4,529,230 | * | 7/1985 | Fatula, Jr. .............................. | 285/353 |
| 4,787,656 | * | 11/1988 | Ryder .................................... | 285/353 |
| 5,234,235 | * | 8/1993 | Worden ................................. | 285/353 |
| 5,346,262 | * | 9/1994 | Liebig .................................... | 285/353 |
| 5,882,042 | * | 3/1999 | Lacoste ................................. | 285/179 |

FOREIGN PATENT DOCUMENTS

| | | | | |
|---|---|---|---|---|
| 675245 | * | 2/1930 | (FR) ...................................... | 285/353 |
| 224021 | * | 11/1924 | (GB) ..................................... | 285/353 |
| 535441 | * | 4/1941 | (GB) ..................................... | 285/353 |
| 801631 | * | 9/1958 | (GB) ..................................... | 285/353 |

* cited by examiner

*Primary Examiner*—Eric K. Nicholson
(74) *Attorney, Agent, or Firm*—Bracewell & Patterson L.L.P.

(57) ABSTRACT

A tapered conic ferrule in accordance with an industry standard is abutted against a male nut. The nut is provided with a length wise passage having an end at a head on the nut. The passage has a radius of curvature to enable the tube to bend, but not sharply so that the tube is not damaged.

7 Claims, 1 Drawing Sheet

NUT WITH CONTROLLED INTERNAL RADIUS

BACKGROUND OF THE DISCLOSURE

This disclosure involves a GC connector assembly. It is a device which is especially intended for use with tubing which connects a gas chromatograph (GC hereafter) to various pieces of test equipment. A gas chromatograph cannot work with a large fluid flow. Stated more precisely, most GC samples are extremely small samples. While it might be possible to obtain a test sample out of a large storage tank at a refinery, to pick an example, most laboratory investigations involve samples and specimens which are extracted from smaller and smaller sources. For instance, practically all biological work involves extracts from living tissue, not necessarily large samples at that. If a five or ten milliliter sample is initially provided, the extracted family of compounds of interest might be measured in the microliter range. To this end, a GC is scaled so that, while very small, it fortunately can provide high quality constituent separation with a throughput which is quite small. Literally, the separated volume is perhaps only parts per million of a sample in the microliter range so that the measured peak of interest output by the GC involves only a few hundred molecules of interest. That, indeed, is uncommonly small.

The GC equipment has to be hooked up to several items to operate. Commonly, there will be a pump for a flow of solvent. At the output end, the GC equipment will connect with some kind of analyzer such as an FID. Often, it will be output to any other small device for test purposes. The GC is normally built with valves, pumps, filters, and other equipment which are all connected together to upstream and downstream devices involving very small tubing and fittings. The tubing has a nominal size of ⅟₁₆ inch, which involves a diameter of 0.0625 inches. Commonly, it is made of stainless so that there is very little surface interaction between the metal of the tubing and the samples which flow through the tubing along with the carrier and discharge or waste gases. To this end, the system is quite small. Even in larger and more ambitious sizes, the tubing commonly will be ⅛ tubing which has an actual size of 0.125 inches. Whether it is either size tubing, the sidewall is normally formed of stainless steel for either size, and is made of sufficient thickness to have mechanical integrity.

Tubing of this sort is often connected and disconnected with the set of fittings to test equipment on the work bench. While an investigation may last only a day or two, and some other investigations will last many hundreds of experiments, the tubing on the work bench in a chemical test laboratory is plumbed to make the connections. These connections normally involve tubing of the sizes noted which connect with fittings. A common assembly technique involves the use of a male nut which is threaded behind a ferrule, and the nut, ferrule, and tubing end are positioned in a fitting detail. The term "detail" identifies an industry standard type of fitting which receives the threaded male nut with a mating set of threads, an internal tapered area for seating the ferrule, and an extending hole terminating in the shoulder. This receives the end of the tubing or the pilot portion of the tubing which extends into the detail. This is normally located in a larger device, being an internally formed cavity having the fitting detail in it. This will be at the base or input manifold of a valve assembly, or a larger assembly which involves the test device. This can be an input port on a pump, GC column base, GC input, input for a mass spectrometer and other test instruments. The fitting detail is often a counterbored assembly which is carefully fabricated so that the housing or manifold body receives the connections time and time again. Often, the fitting detail does not require refinishing for hundreds of connections spanning several years of use of the fitting detail and the structure to which it provides a port or input.

With as many connections and disconnections as are required, there is some risk of work hardening of the metal tubing. Localized stresses placed on the metal tubing are fairly severe to assure an adequate seal. While the total force involved may be small, taking into account the scale of the tubing, the localized stresses are fairly high. One of these stresses involves bending of the tube. In the optimum circumstance, the tube is input in a straight line fashion. However, optimum circumstances do not always happen. Moreover, the conditions that are involved in plumbing the thin tubing vary markedly so that all kinds of problems can arise. Representative plumbing problems include the difficulty of bending the tubing. Often, the fitting detail and nut in it will be jammed against a back splash on a test bench, or some other fixture which mandates that the tubing extend out of the fitting detail and nut, and then turn sharply at an angle. With the present apparatus, this can be done so that the tubing can extend against the back splash without damage. This significantly improves the plumbing and installation of a chemical test procedure equipment. This assists in a component location. This permits the plumed equipment to be jammed against the back splash without worry over damage or breakage of the tubing connections.

BRIEF DESCRIPTION OF THE DRAWINGS

So that the manner in which the above recited features, advantages and objects of the present invention are attained can be understood in detail, more particular description of the invention, briefly summarized above, may be had by reference to the embodiments thereof which are illustrated in the appended drawings.

It is to be noted, however, that the appended drawings illustrate only typical embodiments of the invention and are therefore not to be considered limiting of its scope, for the invention may admit to other equally effective embodiments.

BRIEF DESCRIPTION OF THE PREFERRED EMBODIMENT

Figure 1:
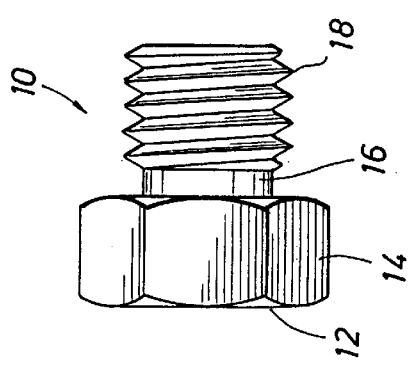
FIG. 1 is the side view of a male nut in accordance with the teachings of the present disclosure.

This disclosure sets forth in FIG. 1 a nut which is used in making tubing connections with small flow lines, typically only a fraction of an inch in diameter where the lines have to connect to or from test instruments. They typically emerge from and extend out of the equipment through a male nut such as the nut shown in FIG. 1. The nut 10 incorporates a head 12 at one end where the head 12 is equipped with flats 14 on the exterior. The flats 14 are formed to an industry standard so that the nut can be engaged by and rotated by a hand tool such as a wrench. The nut includes a shaft or shank which is not threaded, this being illustrated at 16. On the distal exterior, there is a set of threads 18 which conform to some industry standard. In the example given, the threads are 10–32 UNF to pick a representative standard. Other standards can be used with the threads. The threads on the shaft or shank are constructed in accordance with the industry standard.

Figure 3:
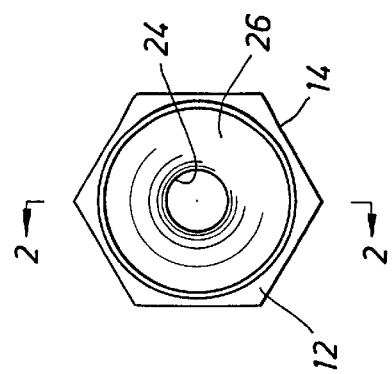
FIG. 3 is an end view of the nut shown in FIGS. 1 and 2.
Figure 2:
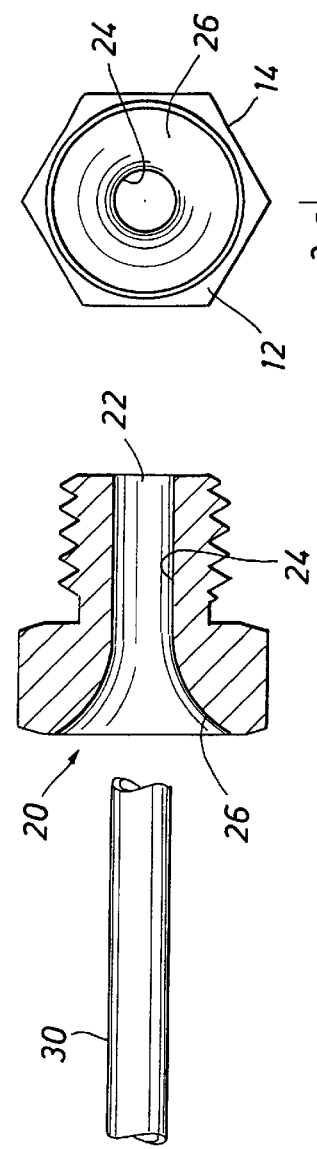
FIG. 2 is a sectional view through the nut of FIG. 1 showing added details of construction.

Going now to FIGS. 2 and 3 considered jointly, it will be observed that a very special radiused hole 20 is formed coaxially through the head of the nut and extends fully through the length of the shaft or shank. The remote end 22 emerges in a coaxial fashion on the interior of the lower end of the nut. Moreover, the male nut is constructed with a drilled through hole 24. The hole 24 is of sufficient length to extend from end to end. It has a constant diameter beginning at the right hand side of FIG. 2. This diameter, however, changes at the open head end 26. The head end 26 is constructed with a radius of curvature. The radius of curvature in this instance is approximately double the diameter of the hole 20. More specifically, if the hole 20 through the bolt has a diameter of one unit, the radius of curvature in this instance is approximately two units. Comparing radii, the radius of the hole 20 is defined as one unit and the radius of curvature is about four units. With that ratio, it will be observed that the opening flares out in a fashion enabling the tubing inserted into the passage to bend without kinking. With a ratio of 4:1 using the bevel radius as the numerator and the radius of the hole as the denominator, it will be observed that bending of metal tubing does not create the likelihood of kinks or breaks in the tubing. Otherwise, there is a risk of sharp bends and pinching. As will be further understood, FIG. 3 shows the opening 20 extending fully through the head of the male nut and to the opposite open end.

Figure 4:
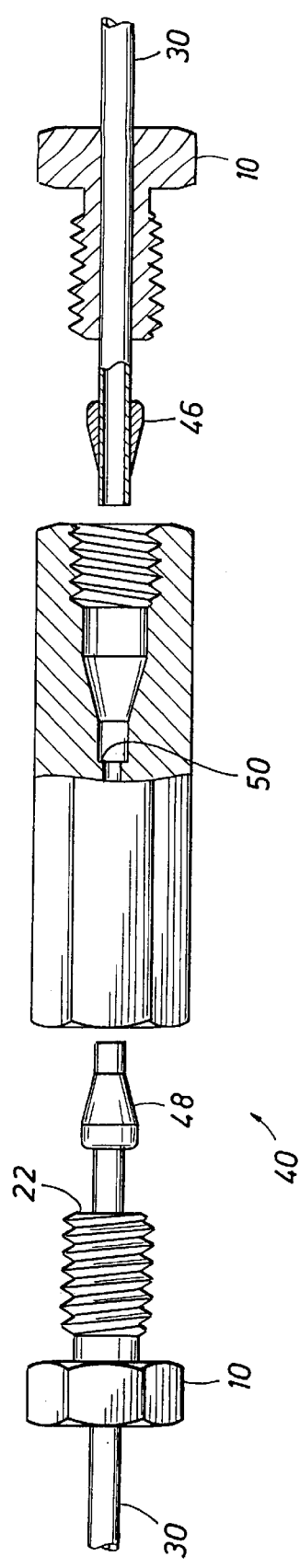
FIG. 4 shows a nut for a fitting detail.

In FIG. 2, a tubing 30 is shown in alignment with the hole 20 which is drilled or formed through the male nut. The tubing 30 represents tubing which is pushed into the opening. As noted, this tubing is preferably 1/16 nominal size tubing. That is the preferred or common dimension. Occasionally, equipment will be plumbed with tubing which is twice the diameter, i.e., 1/8 inch tubing. For that size, the dimensions shown and discussed are preferably doubled so they conform to the large tubing. The tubing which is positioned in the male nut is extended fully through and passes through a ferrule and inserts into the pilot hole of a fitting detail. It jams up against a shoulder. When so positioned, the tubing is then ready for clamping. The male nut is engaged which forces the ferrule with pressure. An example of this is set forth in FIG. 4. FIG. 4 shows how the tubing goes all the way through and shoulders against a remote or distal transverse shoulder. In effect, the tubing 30 is jammed until it bottoms against the shoulder in the fitting detail. That limits the penetration of the tubing to enable it to the pilot length.

By use of hand tools, the male nut is threaded into the fitting detail and shoulders against it, thereby locking at a certain position. This defines the point at which the tubing is held. At the region where the tubing 30 emerges out of the confines of the narrow passage, the tubing at that region is then free to bend. In the past, this opening has been essentially a drilled hole with a small chamber or beveling at the end. That leaves the tubing in condition to be pinched by excessive bending or repeated bending, or both. Bending not only damages the tubing so that a break is observed, but it can also damage the tubing so that it becomes work hardened even though such damage cannot be inspected casually. After all, the tubing in the preferred embodiment is quite small, and visual inspection is difficult to accomplish. To defeat that limitation, the present apparatus positions the tubing so that it is bent to an acceptable radius or curvature which does not run the risk of sharp bends at the nut where it emerges, free in space, from beyond the confines of the passage in the mounting nut 10. So to speak, this defines a support structure for the end of the tubing and the incorporation of the curvature in the passage (see FIG. 2 of the drawings) assures that sharp bends and fatigue breaks are avoided. By avoiding such sharp corners, breaking is avoided. The radius inside the head of the nut allows the user to bend the tube inside the nut more or less than 90° from its original orientation in the detail. Tubing failure can be catastrophic. First, even if the break is partial, not complete, leakage may occur and the fluid flow in the tube will be mixed with atmosphere. Just as importantly, the system fails should the tubing bend and the sharp bend prompts complete breakage. This construction makes a wonderful connection which can be made and remade time and time again. In FIG. 4 of the drawings, the tubing is held so that the nut does not over stress or pinch the tube.

In the present disclosure, FIG. 4 shows the context of the nut. Considering the entire assembly shown in FIG. 4, the assembly as a whole is identified by the numeral 40. It is symmetrical on the left and right; therefore description devoted to either side will suffice for both sides. The tubing 30 is inserted through the passage in the male nut 10. The male nut bears against a ferrule 48. It secures the tubing so that a portion of the tubing extends beyond the end of the ferrule. The tubing bottoms against a shoulder 50 on the inside of the fitting 40. The fitting 40 makes interconnection of one tubing to another. For instance, the tubing 30 on the left can be larger than the tubing on the right. As an alternative need, the fitting 40 can be used to splice together a pair of short tubing members so that greater length is obtained. The tubing 30 extends through the nut 10 previously mentioned. The ferrule 46 on the right is either identical to or different in size or taper compared to the ferrule 48. Both ferrules, however, are constructed in accordance with the teachings of the present disclosure. Both operate in the same fashion.

At the time of installation, each male nut 10 is tightened. As it threads up, it jams the adjacent ferrule into the fitting 40 and pushes the tubing toward the internal transverse shoulder 20. The fitting 40 is constructed to squeeze the ferrules to assure a tight or snug fit. The fitting 40 includes the conforming internal taper which cooperates with the ferrule when placed therein so that the ferrule is able to grip and thereby create hoop stress around the tubing on the interior. It is especially common to use metal tubing. Tubing deformation is controlled so that the fitting gets a good "bite" on the tubing. In other words the bite holds the tubing in place. The term "detail" is normally applied to the dimensions of the internal threads and seats within the fitting 40. The fitting detail, therefore, refers to that which is shown in profile in the sectional cut portion of FIG. 4. Fitting construction is controlled so that the tube is clamped, is held firmly in the fitting 40, and yet is not destroyed so that the interior flow path through the tubing is preserved.

The ferrule of the present disclosure is used in the ordinary fashion. When placed in use, it conforms to the fitting detail in which it is inserted. The fitting detail conforms in accordance with the industry standards for conventional ferrules, male nuts, and other connective equipment. The ordinary procedure is to apply force to the nut which jams the ferrule into the tapered and conforming cavity. It seems to accommodate more readily torquing to a desired tightness on the male nut which drives the ferrule into the fitting detail. For that matter, torquing is done controllably to assure that the fitting detail is not damaged by over driving the ferrule into the cavity. Suffice it to say, this approach helps prevent damage to the detail, ferrule and tube.

While the foregoing is directed to the preferred embodiment, the scope is determined by the claims which follow:

What is claimed is:

1. A tube holding nut positioning a ferrule conforming to a predetermined fitting detail, wherein the nut comprises a head and shaft having an axial passage defining a passage diameter for receiving tubing therethrough of a predetermined tubing diameter and wall thickness, the passage diameter about equal to the tubing diameter, to seal the tubing in a connection at the fitting detail, and wherein the nut head comprises an opening for said passage having a radius of curvature of at least about twice the passage diameter.

2. The apparatus of claim 1 wherein said nut abuts the ferrule to position both nut and ferrule on said tubing without bending said tubing.

3. The apparatus of claim 1 wherein the radius of curvature flairs to the end face of the nut head.

4. The apparatus of claim 3 wherein said nut passage fits around 1/16 inch tubing.

5. The apparatus of claim 3 wherein said nut head connects to said shaft with thread of a predetermine configuration formed thereon.

6. An assembled fitting connection for attachment on the end of a 1/8 or 1/16 inch tube extending through the fitting for connection with a fitting detail wherein the assembly is formed on the end of the tube and comprises a male nut on the tube having a set of threads to enable the male nut to thread into the detail and to seal the tube in the fitting detail with a ferrule positioned at the end of the male nut and around the tube; and wherein the tube is positioned in the fitting by passing through the nut and ferrule to provide sealed flow into the fitting detail, and said nut is constructed with a fitting detail conforming threaded shaft and said shaft has a specified length to thread into the fitting detail and terminates at an encircling tapered conic surface on the nut head and said nut has a central passage through said nut enabling the tubing to bend at the end of the passage at a passage related radius of curvature of at least about twice the diameter of the passage.

7. The apparatus of claim 6 wherein said nut head passage is formed in the head and shaft.

* * * * *